(12) United States Patent
Deak et al.

(10) Patent No.: US 10,238,793 B2
(45) Date of Patent: Mar. 26, 2019

(54) PRECISION SYRINGE PUMP AND MANUFACTURING METHOD THEREOF

(71) Applicant: MultiDimension Technology Co., Ltd., Zhangjiagang (CN)

(72) Inventors: James Geza Deak, Zhangjiagang (CN); Yuqin Jin, Zhangjiagang (CN)

(73) Assignee: MULTIDIMENSION TECHNOLOGY CO., LTD, Zhangjiagang (CN)

( * ) Notice: Subject to any disclaimer, the term of this patent is extended or adjusted under 35 U.S.C. 154(b) by 183 days.

(21) Appl. No.: 15/119,689

(22) PCT Filed: Feb. 12, 2015

(86) PCT No.: PCT/CN2015/072868
§ 371 (c)(1),
(2) Date: Aug. 17, 2016

(87) PCT Pub. No.: WO2015/124081
PCT Pub. Date: Aug. 27, 2015

(65) Prior Publication Data
US 2017/0056581 A1 Mar. 2, 2017

(30) Foreign Application Priority Data
Feb. 20, 2014 (CN) .......................... 2014 1 0058046

(51) Int. Cl.
*A61M 5/145* (2006.01)
*A61M 5/142* (2006.01)
(Continued)

(52) U.S. Cl.
CPC ...... *A61M 5/14216* (2013.01); *A61M 5/1452* (2013.01); *A61M 5/14236* (2013.01);
(Continued)

(58) Field of Classification Search
CPC .................. A61M 2205/3317; A61M 5/14236
See application file for complete search history.

(56) References Cited

U.S. PATENT DOCUMENTS

| 4,435,173 A | 3/1984 | Siposs et al. |
| 8,382,703 B1 | 2/2013 | Abdelaal |
| (Continued) | | |

FOREIGN PATENT DOCUMENTS

| CN | 1266373 | 9/2000 |
| CN | 101745163 | 6/2010 |
| (Continued) | | |

OTHER PUBLICATIONS

"International Application No. PCT/CN2015/072868, International Search Report dated Apr. 29, 2015", (Apr. 29, 2015), 5 pgs.
(Continued)

*Primary Examiner* — Deanna K Hall
(74) *Attorney, Agent, or Firm* — Schwegman Lundberg & Woessner, P.A.

(57) ABSTRACT

A precision syringe pump employing a syringe comprises a motor, a lead screw and a syringe driving head connected to the lead screw. The syringe comprises a cylinder and a plunger. The motor drives the lead screw to rotate clockwise or counterclockwise to drive the syringe driving head and push the plunger to move within the cylinder. The syringe pump further comprises: a magnetoresistive sensor, at least one permanent magnet and an MCU, the at least one permanent magnet being located on the lead screw and rotating therewith; the magnetoresistive sensor can sense the magnetic field generated by the at least one permanent magnet; the input end of the MCU is connected to the magnetoresistive sensor, and the output end of the MCU is connected to the motor; the MCU receives signals from the magnetoresistive sensor and controls, according to the signal feedback, the direction and velocity of the lead screw rotated
(Continued)

by the motor. The precision syringe pump of the present invention is characterized by high sensitivity, high reliability, low power consumption and low cost, and is convenient to use.

20 Claims, 4 Drawing Sheets

(51) Int. Cl.
*A61M 5/168* (2006.01)
*A61M 5/172* (2006.01)

(52) U.S. Cl.
CPC ...... *A61M 5/1684* (2013.01); *A61M 5/16886* (2013.01); *A61M 5/172* (2013.01); *A61M 2205/18* (2013.01); *A61M 2205/3317* (2013.01); *A61M 2205/3365* (2013.01); *A61M 2205/3389* (2013.01); *A61M 2207/00* (2013.01)

(56) References Cited

U.S. PATENT DOCUMENTS

| | | | | |
|---|---|---|---|---|
| 9,677,555 | B2* | 6/2017 | Kamen | ............ F04B 43/1261 |
| 2002/0043951 | A1 | 4/2002 | Moberg | |
| 2003/0233069 | A1 | 12/2003 | Gillespie, Jr. et al. | |
| 2010/0050731 | A1 | 3/2010 | Granig et al. | |
| 2010/0118447 | A1 | 5/2010 | Hammerschmidt et al. | |
| 2010/0211003 | A1* | 8/2010 | Sundar | ............ A61M 5/16813 604/67 |
| 2011/0301566 | A1 | 12/2011 | Schaefer | |
| 2013/0281965 | A1 | 10/2013 | Kamen et al. | |
| 2017/0028124 | A1 | 2/2017 | Deak et al. | |

FOREIGN PATENT DOCUMENTS

| | | |
|---|---|---|
| CN | 201692426 | 1/2011 |
| CN | 202113388 | 1/2012 |
| CN | 102614565 | 8/2012 |
| CN | 103191486 | 7/2013 |
| CN | 203163674 | 8/2013 |
| CN | 103656797 | 3/2014 |
| CN | 103768679 | 5/2014 |
| CN | 103920207 | 7/2014 |
| CN | 203802882 | 9/2014 |
| CN | 203885937 | 10/2014 |
| DE | 29622313 | 3/1997 |
| EP | 0390388 | 10/1990 |
| EP | 0465267 | 1/1992 |
| EP | 2682772 | 1/2014 |
| JP | H0584296 | 4/1993 |
| WO | WO-2004113928 | 12/2004 |
| WO | WO-2015/124081 | 8/2015 |
| WO | WO-2015158230 | 10/2015 |

OTHER PUBLICATIONS

"U.S. Appl. No. 15/304,251, Non Final Office Action dated Apr. 17, 2018", 10 pgs.
"Chinese Application No. 201410058046.9, First Office Action dated Apr. 3, 2015", (Apr. 3, 2015), 8 pgs.
"Chinese Application No. 201410058046.9, Second Office Action dated Dec. 29, 2015", (Dec. 29, 2015), 8 pgs.
"Chinese Application No. 201410146550.4, First Office Action dated Aug. 18, 2015", (Aug. 18, 2015), 8 pgs.
"Chinese Application No. 201410146550.4, Second Office Action dated Feb. 26, 2016", (Feb. 26, 2016), 7 pgs.
"European Application No. 15751470.4, Extended European Search Report dated Sep. 29, 2017", (Sep. 29, 2017), 6 pgs.
"European Application No. 15780592.0, Extended European Search Report dated Nov. 15, 2017", (Nov. 15, 2017), 9 pgs.
"International Application No. PCT/CN2015/076428, International Search Report and Written Opinion dated Jun. 29, 2015", (Jun. 29, 2015), 13 pgs.

\* cited by examiner

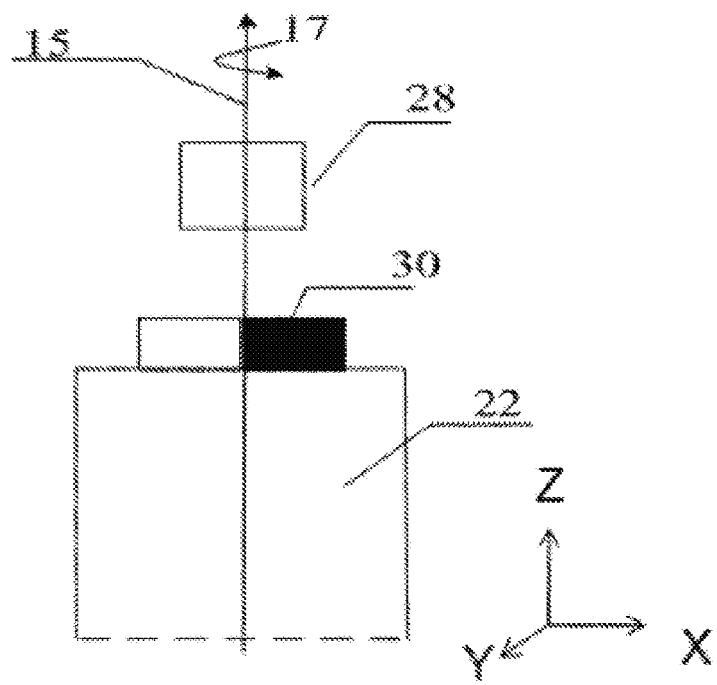
FIG. 2A
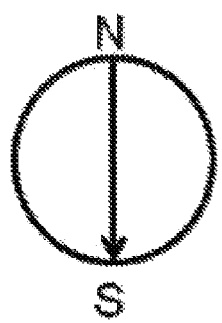 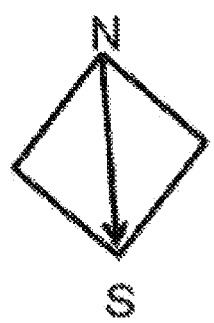 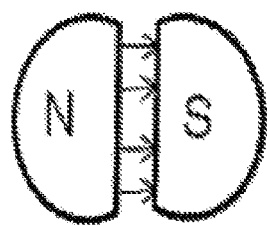
FIG. 2B        FIG. 2C        FIG. 2D
FIG. 2

PRECISION SYRINGE PUMP AND MANUFACTURING METHOD THEREOF

PRIORITY CLAIM TO RELATED APPLICATIONS

This application is a U.S. national stage application filed under 35 U.S.C. § 371 from International Application Serial No. PCT/CN2015/072868, which was filed 12 Feb. 2015, and published as WO2015/124081 on 27 Aug. 2015, and which claims priority to Chinese Application No. 201410058046.9, filed 20 Feb. 2014, which applications and publication are incorporated by reference as if reproduced herein and made a part hereof in their entirety, and the benefit of priority of each of which is claimed herein.

TECHNICAL FIELD

The present invention relates to a medical device, and in particular, to a syringe pump for infusion.

BACKGROUND ART

In clinical use, infusion pumps allow automatically infusing liquid drugs or nutrients to patients intravenously at a set speed within a relatively longer time, which reduces the workload of medical staff and improves the security of infusion. According to different working principles, the infusion pumps are divided into different types, among which capacity pumps and syringe pumps are common. The capacity pumps can be driven by peristaltic pumps; and the syringe pumps can be driven by lead screw pumps. A motor drives a lead screw to rotate, changes rotational motion into linear motion, and pushes a plunger to inject liquid in a syringe into a patient's vein through a nut connected with the plunger. The precision of an infusion speed of the syringe pumps is higher than that of the capacity pumps, of which an error is about ±5%. However, in some clinical applications, as intravenous injection for new babies and insulin injection for diabetic patients, it is necessary to further improve the precision of the infusion speed of the syringe pumps. During infusion, it is also necessary to know the position of the plunger in the syringe. A common practice is to use a step motor, and it is also feasible to use a linear or rotating potentiometer or an optical decoder to control the infusion speed, but these methods still have problems of low precision, poor reliability and high manufacturing cost.

SUMMARY

With respect to the problems of low precision and poor reliability existing in the existing syringe, the present invention adopts the following technical solution:

The invention discloses a syringe pump employing a syringe, the syringe comprising a cylinder and a plunger, the syringe pump comprising a motor, a lead screw and a syringe driving head connected to the lead screw, and the motor driving the lead screw to rotate clockwise or counterclockwise to drive the syringe driving head and push the plunger to move within the cylinder; wherein the syringe pump further comprises:

at least one permanent magnet, the at least one permanent magnet being located on the lead screw and rotating therewith;

a magnetoresistive sensor that can sense a magnetic field generated by the at least one permanent magnet; and an MCU that receives signals from the magnetoresistive sensor and controls, according to signal feedback of the magnetoresistive sensor, the direction and velocity of the lead screw rotated by the motor.

Preferably, the magnetoresistive sensor is a biaxial rotary magnetic sensor or two orthogonal uniaxial rotary sensors.

Preferably, the magnetoresistive sensor is a uniaxial or biaxial linear magnetic sensor.

Preferably, the magnetoresistive sensor is a Hall, AMR, GMR or TMR sensor.

Preferably, central axes of the at least one permanent magnet and the lead screw pass through the center of the magnetoresistive sensor.

Preferably, the magnetoresistive sensor is in the vicinity of the at least one permanent magnet.

Preferably, the at least one permanent magnet is an integrated permanent magnet or a separated permanent magnet, and is disc-shaped, annular or square; the integrated permanent magnet or separated permanent magnet is located on the same end of the lead screw as the motor or the other end of the lead screw.

Preferably, two permanent magnets are provided, each of the permanent magnets has a plurality of different magnetic poles, and the two permanent magnets are respectively located on two ends of the lead screw or placed on the same end of the lead screw in series.

Preferably, the permanent magnet is magnetized along the diameter or the diagonal line of the permanent magnet or along a direction vertical to a long axis of the lead screw, and an internal magnetization direction of the permanent magnet is perpendicular to the long axis of the lead screw.

Preferably, a surface area of the magnetoresistive sensor in an XY plane is less than a cover area of the permanent magnet in the XY plane.

Preferably, the MCU comprises a magnetoresistive sensor information management unit for converting a rotating speed of the lead screw to an infusion speed of the syringe.

Preferably, the magnetoresistive sensor information management unit comprises a motor rotation angle counting unit, a lead screw position unit and/or a plunger position unit, a solution volume unit and a flow rate unit.

Preferably, the MCU comprises a comparator for comparing the infusion speed of the syringe with a set infusion speed, and the MCU adjusts the rotating speed of the lead screw according to a comparison result.

Preferably, the syringe pump comprises a motor controller and an alarm, wherein the MCU controls the rotating direction and the rotating speed of the motor through the motor controller, and the alarm is connected with the motor controller.

Preferably, the syringe pump comprises at least one guide rod parallel to the lead screw, wherein one end of the syringe driving head is placed on the guide rod in a manner that permits it to slide, the lead screw passes through a hole with screw threads which is located on the other end of the syringe driving head, the guide rod is fixed onto a base, and the lead screw is rotatably fixed onto the base.

Preferably, the motor is a DC motor or a step motor.

Preferably, the syringe pump comprises a mechanical transmission device connecting the motor and the lead screw; the mechanical transmission device being at least one gear and a reduction gear or a pulley and a transmission belt.

The invention discloses a method of manufacturing the syringe pump. The syringe pump comprises a motor, a lead screw and a syringe driving head connected to the lead screw, and the motor drives the lead screw to rotate clockwise or counterclockwise to drive the syringe driving head and push the plunger to move within the cylinder, wherein at least one permanent magnet is disposed on the lead screw, making the permanent magnet rotate with the lead screw;

the magnetoresistive sensor is disposed in a position on the syringe pump where a magnetic signal generated by the at least one permanent magnet can be received; and an MCU for controlling the direction and velocity of the lead screw rotated by the motor according to magnetic signal feedback is installed on the syringe pump.

Preferably, the magnetoresistive sensor is a Hall, AMR, GMR or TMR sensor.

In the syringe pump driven by a lead screw pump of the present invention, a magnetoresistive sensor and a Micro Control Unit (MCU) are employed to feed back and control an infusion speed and monitor the position of the plunger in the syringe, which replaces the manner of controlling the infusion speed with a step motor. Precision of controlling the infusion speed by the step motor depends on the number of phases and the number of beats, the more the number of phases and the number of beats are, the higher the precision is. At a low speed, the step motor is prone to low frequency vibration. If the starting frequency is too high or the load is too large, it is easy to lead to a step loss or rotation blockage, and when the step motor stops, it is easy to lead to overshoot due to overhigh rotating speed. In the present invention, another motor can be used to replace the step motor, and can also be used together with the step motor, which improves precision and reliability of the infusion speed of the syringe pump. According to the present invention, an ordinary DC motor instead of an expensive step motor may be used, which thus reduces the cost of the syringe pump. In addition, application of the magnetoresistive sensor with low power consumption may also reduce the power consumption of the syringe pump and decrease the charging frequency, which is an important improvement for syringe pumps generally powered by batteries, and facilitates the use. To sum up, the precision syringe pump of the present invention is characterized by high sensitivity, high reliability, low power consumption and low cost, and is convenient to use.

The above description is merely a summary of the technical solution of the present invention. In order to describe the technical measures of the present invention more clearly and implement the present invention according to the contents of the specification, the present invention is described in detail below in combination with embodiments and with reference to the accompanying drawings. Specific implementation of the present invention is given in detail through the following embodiments.

BRIEF DESCRIPTION OF THE DRAWINGS

FIG. 2 is a schematic sectional view showing a position relationship between a magnetoresistive sensor and a permanent magnet and a schematic view showing a magnetization direction of the permanent magnet;

DETAILED DESCRIPTION

Figure 1:
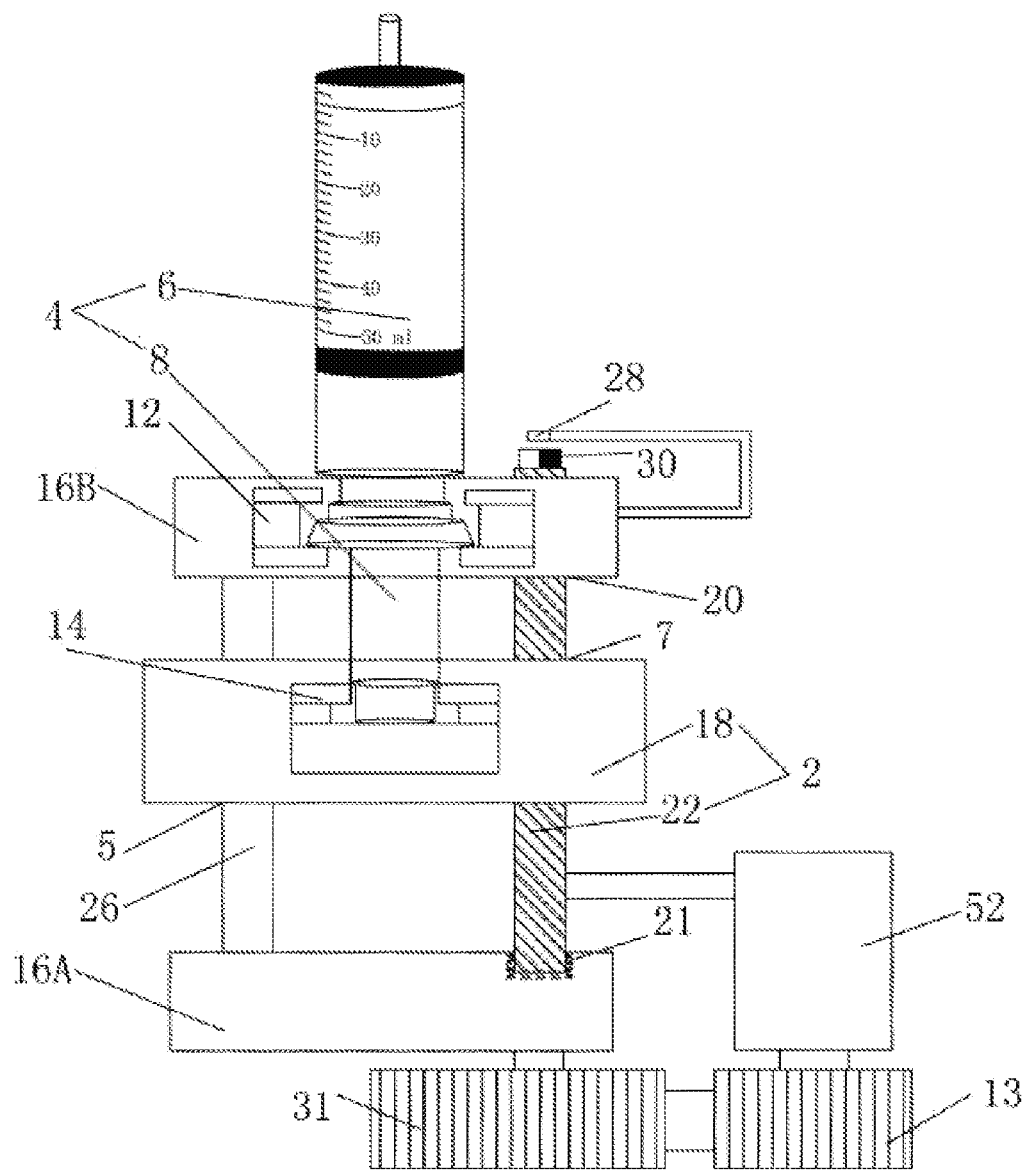
FIG. 1 is a top view of a syringe pump.
Figure 3:
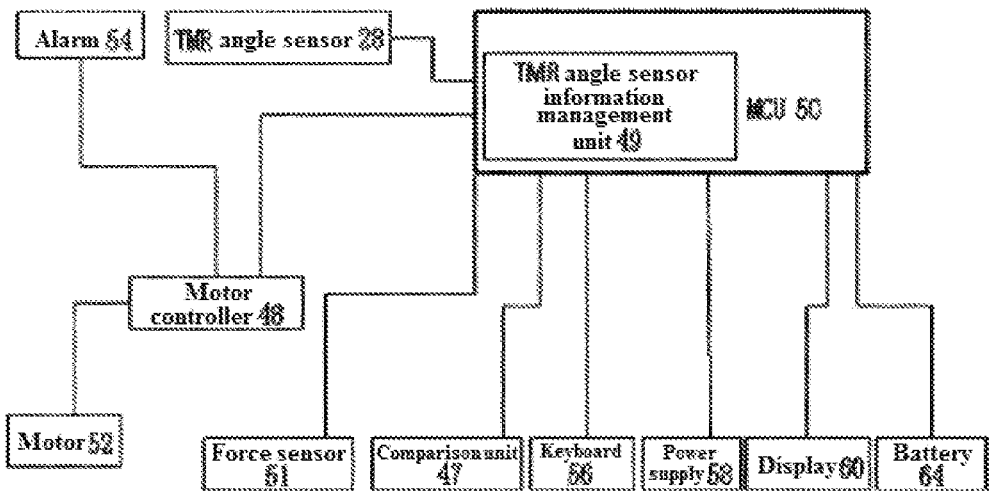
FIG. 3 is a control schematic diagram of an MCU.

FIG. 1 is a top view of a syringe pump 2. A syringe pump 2 that can employ a syringe 4 comprises a motor 52, a lead screw 22 and a syringe driving head 18. The syringe 4 comprises a cylinder 6 and a plunger 8. The motor 52 drives the lead screw 22 to rotate clockwise or counterclockwise to drive the syringe driving head 18 and push the plunger 8 to move within the cylinder 6; the syringe pump 2 further comprises a magnetoresistive sensor 28, at least one permanent magnet 30 and an MCU 50; the permanent magnet 30 is located on the lead screw 22, and rotates therewith; the magnetoresistive sensor 28 can sense a magnetic field generated by the permanent magnet 30; an input end of the MCU 50 is connected with the magnetoresistive sensor 28, and an output end is connected with the motor 52; the MCU 50 receives signals from the magnetoresistive sensor 28 and, according to the signal feedback, controls the direction and velocity of the lead screw 22 rotated by the motor 52.

One end of the lead screw 22 connected with the motor 52 is rotatably fixed onto a front base 16A through a bearing 21, and the other end passes through a hole 20 without screw threads on a rear base 16B to be rotatably fixed onto the rear base 16B. In order to drive the syringe driving head 18, the lead screw 22 passes through a hole 7 with an internal thread on the syringe driving head 18 which matches an external thread of the lead screw 22. The motor 52 drives the lead screw 22 to rotate clockwise or counterclockwise in the hole 7 in the syringe driving head 18 through a mechanical transmission device that can change a rotating speed, for example, one or more reduction gears 13 and gears 31, so that the lead screw 22 drives the syringe driving head 18 to linearly move repeatedly. In order to reduce the cost, it is also feasible to replace the gears 31 and the reduction gears 13 with a pulley and a transmission belt.

A guide rod 26 playing a role of stabilization and guide passes through a hole 5 without screw threads on the other end of the syringe driving head 18 and is disposed in parallel to the lead screw 22. There may be one or more guide rods 26 playing a role of stabilization, of which the two ends are respectively fixed onto the front base 16A and the rear base 16B.

Without use of the guide rod 26, the syringe driving head 18 may also move along a slide rail which is parallel to the lead screw 22.

The motor 52 may be a DC motor, an AC motor, a step motor, a servo motor or the like.

The syringe driving head 18 is provided with a pair of plunger clamps 14 that can fix and hold the plungers 8 of the syringes 4 with different diameters; therefore, when the lead screw 22 rotates in the hole 7 of the syringe driving head 18, the syringe driving head 18 makes linear motion along the direction of the guide rod 26, so as to push or pull the plunger 8 to move in the cylinder 6. A pair of cylinder clamps 12 is mounted on the rear base 16B, which can fix the cylinders 6 of the syringes 4 with different diameters.

FIG. 2 is a schematic sectional view showing a position relationship between a magnetoresistive sensor and a permanent magnet and a schematic view showing a magnetization direction of the permanent magnet. The permanent magnet 30 rotates with the lead screw 22 along a rotating direction 17, while the magnetoresistive sensor 28 is stationary. The magnetoresistive sensor 28 is a biaxial rotary magnetic sensor or two orthogonal uniaxial rotary sensors, and may also be a uniaxial linear sensor or a biaxial linear sensor. The existing magnetoresistive sensing elements include Hall elements, Anisotropic Magneto Resistance (AMR) elements or Giant Magneto Resistance (GMR) elements and Tunnel Magneto Resistance (TMR) elements. The TMR technology is the most advanced and is also a preferred technology of the present invention, but other magnetoresistive sensing elements may also be used for the magnetoresistive sensor 28.

The permanent magnet 30 is an integrated or separated permanent magnet, and is disc-shaped, annular or square. Two permanent magnets 30 may be provided, each of which has multiple different magnetic poles. FIGS. 2B, 2C and 2D show that the permanent magnet 30 is disc-shaped, square, and is a separated permanent magnet and show some respective possible magnetization directions, but do not show all possible shapes and magnetization directions. The aforementioned permanent magnet 30 has a thickness that satisfies a suitable application condition. A surface area of the magnetoresistive sensor 28 in an XY plane is less than a cover area of the permanent magnet 30 in the XY plane. The lead screw 22 has a long axis 15 in a Z-axis direction, and the long axis 15 is perpendicular to the XY plane, passes through the center of the permanent magnet 30, and is coaxial with the permanent magnet 30. Central axes of the permanent magnet 30 and the lead screw 22 pass through the center of the magnetoresistive sensor 28. The permanent magnet 30 is magnetized along a diameter or a diagonal direction, and a magnetization direction thereof is perpendicular to the Z-axis direction or the long axis direction of the lead screw 22. The disc-shaped and annular permanent magnets are magnetized along the diameter direction, and the square permanent magnets are magnetized along the diagonal direction. The permanent magnets may also be magnetized along a direction perpendicular to the long axis of the lead screw. The permanent magnet 30 may be located on one end of the lead screw 22 away from the motor 52, and may also be on the same end therewith. If two permanent magnets 30 are provided, the two permanent magnets are respectively located on two ends of the lead screw 22 or placed on the same end of the lead screw 22 in series. The magnetoresistive sensor 28 is in the vicinity of the permanent magnet 30, and may also be away from the permanent magnet 30. If the two permanent magnets 30 are placed on the same end of the lead screw 22 in series, the magnetoresistive sensor 28 may be in the vicinity of the lead screw 22 and may also be away from the lead screw 22.

The permanent magnet 30 has a rotational phase angle α during rotation. During operation, the magnetoresistive sensor 28 forms sine and cosine to output a rotational magnetic field phase angle f formed between a detection magnetic field component of the permanent magnet 30 and a sensitive axis of the magnetoresistive sensor 28. Only when a linear relationship formed between a and f satisfies one-to-one correspondence within a range of 0 to 360°, can a position relationship between the rotational magnetic field phase angle f detected by the magnetoresistive sensor 28 and the rotational phase angle a of the permanent magnet 30 correspond to each other. The magnetoresistive sensor 28 should be disposed in a detection region of the permanent magnet 30 that can satisfy the foregoing requirements.

Figure 4:
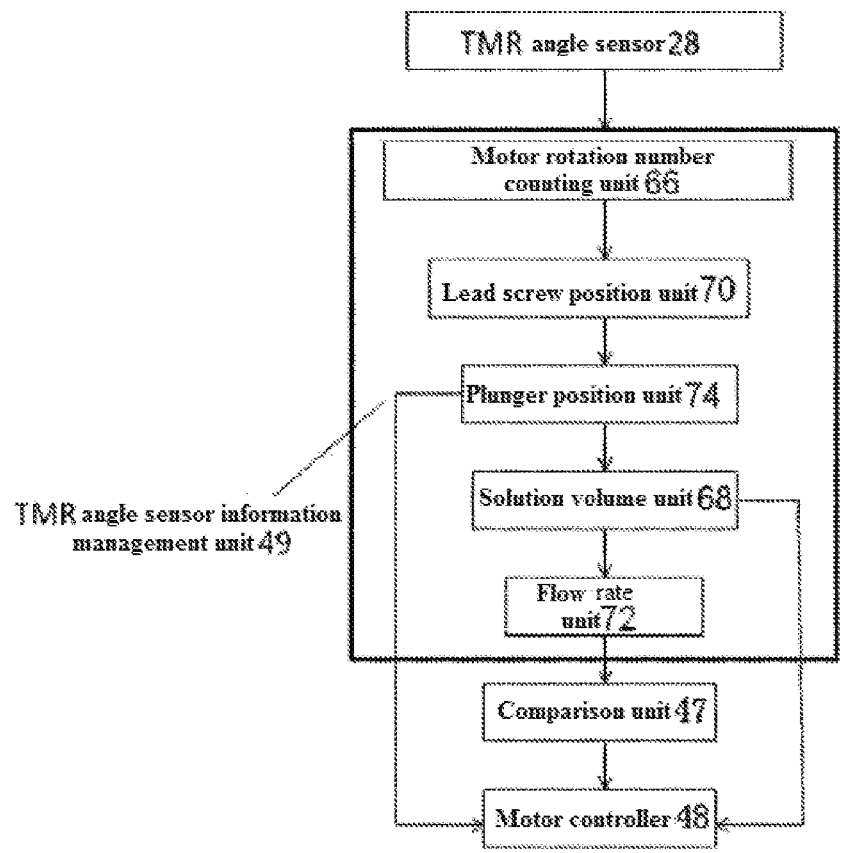
FIG. 4 is a schematic diagram of a magnetoresistive sensor information management unit.

FIG. 4 is a control schematic diagram of an MCU 50. The syringe pump 2 comprises the MCU 50, which receives signals from the magnetoresistive sensor 28 and controls a rotating direction and velocity of the motor 52 through a motor controller 48. In addition, the MCU 50 is connected with an operating keyboard 56, a display 60 and a battery 64.

The motor controller 48 monitors an output signal of the magnetoresistive sensor 28, and is connected with an alarm 48. If a preset position and flow rate are found, the motor controller 48 will activate the alarm 54.

The MCU 50 displays information that a user of the syringe pump is required to know on the display 60. The user can also communicate with the syringe pump 2 through the keyboard 56 connected with the MCU 50. The MCU 50 may also be connected with a force sensor 51 which can detect a force applied to the syringe 4, detect possible blockage and ensure normal infusion, and when the force is over a set value, the force sensor 51 will activate the alarm 54 through the motor controller 48.

The battery 64 provides electric power required by electrical elements and the motor, however, the syringe pump 2 can also use an AC power supply.

Figure 5:
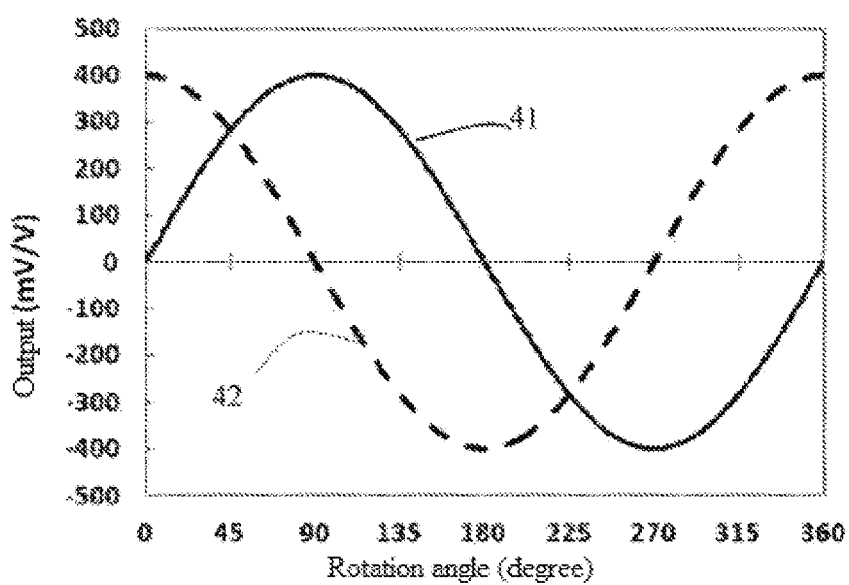
FIG. 5 is a conversion curve.

The MCU comprises a magnetoresistive sensor information management unit 49 for converting a rotating speed of the lead screw 22 to an infusion speed of the syringe. FIG. 5 shows the function of the magnetoresistive sensor information management unit 49 in the MCU 50. The magnetoresistive sensor information management unit 49 comprises a motor rotation angle counting unit 66, a lead screw position unit 70, a plunger position unit 74, a solution volume unit 68, a flow rate unit 72 and a comparison unit 47, and a conversion table of infusion volumes of the syringes 4 with different diameters and the positions of the plungers 8 in the cylinders 6, a conversion table of the positions of the plungers 8 of the syringes 4 with different diameters in the cylinders 6 and the positions of the lead screw 22 and an algorithm of the rotation angle of the lead screw 22 and the positions of the lead screw 22 are preset therein.

When the syringe pump 2 is used, it is necessary to calibrate the syringe pump 2. The MCU 50 can calibrate the syringe pump 2 according to the set program, including all the conversion tables described above, and can calculate infusion volume and velocity. The plunger 8 moves with the rotation of the lead screw 22, and according to the signals from the magnetoresistive sensor 28, the motor rotation angle counting unit 66 records rotation angle and time of the lead screw 22. According to the rotation angle of the lead screw 22 and an algorithm of the rotation angle of the lead screw 22 and a translation position of the lead screw 22 preset in the MCU 50, distance of linear movement of lead screw=(rotation angle)*(longitudinal thread pitch)

the lead screw position unit 70 can calculate the position of the lead screw 22 or the linear distance of its movement in the Z-axis direction; at the same time, according to the conversion table of the position of the lead screw 22 and the positions of the plungers 8 of the syringes 4 with different diameters in the cylinders, the plunger position unit 74 can know the position of the plunger 8 in the cylinder 6; further, the solution volume unit 68 can know the infusion volume according to the conversion table of the volumes of the syringes 4 with different diameters and the positions of the plungers 8 in the cylinders 6; and the flow rate unit 72 can calculate the infusion speed according to the infusion volume and time described above. If a conversion table of rotation angles of the lead screw 22 and the infusion volumes of the syringes 4 with different diameters is preset, the flow rate unit 72 can calculate the infusion speed more quickly according to the conversion table and the rotation angle and time of the lead screw 22 recorded by the motor rotation angle counting unit 66. The MCU further comprises a comparator 47 for comparing the measured infusion speed with a preset infusion speed, and when the measured infusion speed over-deviates or under-deviates from the preset infusion speed, the MCU 50 will instruct the motor controller 48 to adjust the rotating direction and speed of the motor 52. The MCU 50 will instruct the motor controller 48 to adjust the rotating direction and speed of the motor 52 according to the position of the plunger 8 in the cylinder 6 provided by the plunger position unit 74 or according to data of the infusion volume provided by the solution volume unit 68.

A calibration process of the syringe pump 2 is as follows: an empty syringe 4 is disposed on the syringe pump 2; the magnetoresistive sensor information management unit 49 records the position of the plunger 8 in the cylinder 6 measured by the magnetoresistive sensor 28; a known volume of liquid with is then added into the syringe 4; the value of the volume is input into the MCU 50; and the magnetoresistive sensor information management unit 49 can obtain a relationship between the volume of the liquid and the position of the plunger 8 in the cylinder 6 and a relationship between the volume of the liquid and the position of the lead screw 22, and calculate a calibration parameter.

When the step motor is used, in addition that the motor 52 has a function of adjusting the rotating speed of the motor, the MCU 50 can further regulate the speed of the motor 52 according to signal feedback of the magnetoresistive sensor 28 through the motor controller 48, which can thus make the infusion speed more precise.

FIG. 5 is a conversion curve. When the permanent magnet 30 rotates with the lead screw 22 in a rotating direction 17, curves of X-axis and Y-axis magnetic field components detected by the magnetoresistive sensor 28 as a function of the rotation angle are as shown in curves 41 and 42 in FIG. 4 respectively. The magnetoresistive sensor 28 converts a magnetic field amplitude generated by the permanent magnet 30 to an analog voltage signal, and the obtained analog voltage signal can be output directly, and can also be converted to a digital signal through an analog to digital conversion circuit (ADC) and then output. The rotation angle of the permanent magnet 30, that is, the rotation angle of the lead screw 22, can be known according to the output signal.

A method for manufacturing the syringe pump 2 is provided. The syringe pump 2 comprises a motor 52, a lead screw 22 and a syringe driving head 18 connected to the lead screw 22, wherein the motor 52 drives the lead screw 22 to rotate clockwise or counterclockwise to drive the syringe driving head 18 and push the plunger 8 to move within the cylinder 6. The permanent magnet 30 is disposed on the lead screw 22, making the permanent magnet 30 rotate with the lead screw 22; the magnetoresistive sensor 28 is disposed in a position on the syringe pump 2 where a magnetic signal generated by the permanent magnet 30 can be received; and an MCU 50 which controls the direction and velocity of the lead screw 22 rotated by the motor according to the magnetic signal feedback is installed on the syringe pump 2. The magnetoresistive sensor 28 is a Hall, AMR, GMR or TMR sensor.

The above descriptions are merely preferred examples of the present invention, but are not intended to limit the present invention. For persons skilled in the art, the present invention may have various modifications and changes. Implements in the present invention may also be combined and changed differently. Any modification, equivalent replacement, improvement and the like made within the spirit and principle of the present invention shall be included in the protection scope of the present invention.

The invention claimed is:

1. A syringe pump for a syringe having a cylinder and a plunger, the syringe pump comprising:
   a motor;
   a lead screw;
   a syringe driving head connected to the lead screw, wherein the syringe driving head is configured to hold the plunger of the syringe, and the motor is configured to rotate the lead screw clockwise or counterclockwise to drive the syringe driving head and push the plunger to move within the cylinder of the syringe;
   at least one permanent magnet located on the lead screw and configured to rotate with the lead screw;
   a sensor configured to sense a magnetic field generated by the at least one permanent magnet; and
   a micro control unit (MCU) configured to receive signals from the magnetoresistive sensor and control a direction and velocity of the lead screw rotated by the motor based on the received signals from the sensor.

2. The syringe pump according to claim 1, wherein the sensor includes a biaxial rotary magnetic sensor or two orthogonal uniaxial rotary sensors.

3. The syringe pump according to claim 1, wherein the sensor includes a uniaxial or biaxial linear magnetic sensor.

4. The syringe pump according to claim 1, wherein the sensor includes a Hall, AMR, GMR or TMR sensor.

5. The syringe pump according to claim 1, wherein central axes of the at least one permanent magnet and the lead screw pass through a center of the sensor.

6. The syringe pump according to claim 1,
   wherein the at least one permanent magnet is an integrated permanent magnet or a separated permanent magnet, and is disc-shaped, annular or square; and
   wherein the integrated permanent magnet or separated permanent magnet is on the same end of the lead screw as the motor or the other end of the lead screw.

7. The syringe pump according to claim 1, wherein:
   the at least one permanent magnet includes two permanent magnets,
   each of the two permanent magnets has a plurality of different magnetic poles, and
   the two permanent magnets are respectively located on two ends of the lead screw or placed on the same end of the lead screw in series.

8. The syringe pump according to claim 6, wherein the at least one permanent magnet is magnetized along a diameter or a diagonal line of the permanent magnet or along a direction vertical to a long axis of the lead screw, and an internal magnetization direction of the permanent magnet is perpendicular to the long axis of the lead screw.

9. The syringe pump according to claim 1, wherein a surface area of the sensor in an XY plane is less than a cover area of the at least one permanent magnet in the XY plane.

10. The syringe pump according to claim 1, wherein the MCU comprises a sensor information management unit for converting a rotating speed of the lead screw to an infusion speed of the syringe.

11. The syringe pump according to claim 10, wherein the sensor information management unit comprises:
   a motor rotation angle counting unit;
   at least one of a lead screw position unit or a plunger position unit;
   a solution volume unit; and
   a flow rate unit.

12. The syringe pump according to claim 1, wherein the MCU comprises a comparator configured to provide a comparison result by comparing an infusion speed of the syringe with a set infusion speed, and the MCU is configured to adjust a rotation speed of the lead screw according to the comparison result.

13. The syringe pump according to claim 1, wherein the syringe pump further comprises a motor controller and an alarm, wherein the MCU is configured to control a rotation direction and a rotation speed of the motor through the motor controller, and the alarm is connected with the motor controller.

14. The syringe pump according to claim 1, wherein:
the syringe pump further comprises at least one guide rod parallel to the lead screw,
one end of the syringe driving head is slidingly connected onto the guide rod,
the lead screw passes through a hole with screw threads which is located on the other end of the syringe driving head,
the guide rod is fixed onto a base, and
the lead screw is rotatably fixed onto the base.

15. The syringe pump according to claim 1, wherein the motor is a DC motor or a step motor.

16. The syringe pump according to claim 1, further comprising a mechanical transmission device connecting the motor and the lead screw wherein the mechanical transmission device includes:
at least one gear and a reduction gear; or
a pulley and a transmission belt.

17. A method of manufacturing a syringe pump comprising a motor, a lead screw, and a syringe driving head connected to the lead screw, wherein the motor driving the lead screw is configured to rotate the lead screw clockwise or counterclockwise to drive the syringe driving head and push the plunger to move within the cylinder, wherein the method comprises:
positioning at least one permanent magnet on the lead screw such that the at least one permanent magnet rotates with the lead screw;
operably positioning a magnetoresistive sensor in a position on the syringe pump to sense a magnetic signal generated by the at least one permanent magnet; and
operably connecting a micro control unit (MCU) to control rotation direction and velocity of the lead screw rotated by the motor based on the sensed magnetic signal.

18. The method of manufacturing the syringe pump according to claim 17, wherein the sensor includes a Hall, AMR, GMR or TMR sensor.

19. A syringe pump for a syringe having a cylinder and a plunger, the syringe pump comprising:
a motor;
a lead screw;
a syringe driving head connected to the lead screw, wherein the syringe driving head is configured to hold the plunger of the syringe, and the motor is configured to rotate the lead screw clockwise or counterclockwise to drive the syringe driving head and push the plunger to move within the cylinder of the syringe;
at least one permanent magnet located on the lead screw and configured to rotate with the lead screw;
a magnetoresistive sensor configured to sense a magnetic field generated by the at least one permanent magnet, wherein the magnetoresistive sensor includes an AMR sensor, a GMR sensor or a TMR sensor, wherein a central axis of the at least one permanent magnet and a central axis of the lead screw pass through a center of the sensor; and
a micro control unit (MCU) configured to receive signals from the magnetoresistive sensor and control a direction and velocity of the lead screw rotated by the motor based on the received signals from the sensor, wherein the MCU is configured to monitor a position of the lead screw or the plunger in the syringe, and control an infusion speed of the syringe.

20. The syringe pump of claim 19, further comprising a base and at least one guide rod parallel to the lead screw, wherein:
the syringe driving head has one end slidingly connected onto the guide rod and has another end with a hole having screw threads through which the lead screw passes;
the guide rod is fixed onto the base, and
the lead screw is rotatably fixed onto the base.

* * * * *